United States Patent [19]

Laskody

[11] Patent Number: 4,804,374
[45] Date of Patent: Feb. 14, 1989

[54] ANCHOR DEVICE FOR GASTROINTESTINAL TUBE

[76] Inventor: Richard J. Laskody, 8808 NW. 3rd Pl., Coral Springs, Fla. 33065

[21] Appl. No.: 133,846

[22] Filed: Dec. 16, 1987

[51] Int. Cl.$^4$ .............................................. A61M 25/00
[52] U.S. Cl. ............................ 604/180; 128/DIG. 26
[58] Field of Search ............... 604/180; 128/DIG. 26, 128/207.18

[56] References Cited

U.S. PATENT DOCUMENTS

| | | | |
|---|---|---|---|
| 3,046,989 | 7/1962 | Hill | 128/DIG. 26 |
| 4,120,304 | 10/1978 | Moor | 128/DIG. 26 |
| 4,331,143 | 5/1982 | Foster | 128/DIG. 26 |

Primary Examiner—Stephen C. Pellegrino
Attorney, Agent, or Firm—John Cyril Malloy

[57] ABSTRACT

A device to anchor or mount a gastrointestinal tube in its intended operative position relative to the nose of a patient including a mounting member securing the remainder of the assembly to the nose, a securement structure removably attached to the tube and an elastic material connecting element attached at opposite ends thereof to the mounting member and the securement element so as to allow retained displacement of the tube, within certain dimensional limits relative to the nose and thereby accommodate normal movement of the patient, the tube and further allow adjustment, by medical personnel of the tube into and out of a preferred location.

9 Claims, 1 Drawing Sheet

U.S. Patent Feb. 14, 1989 4,804,374
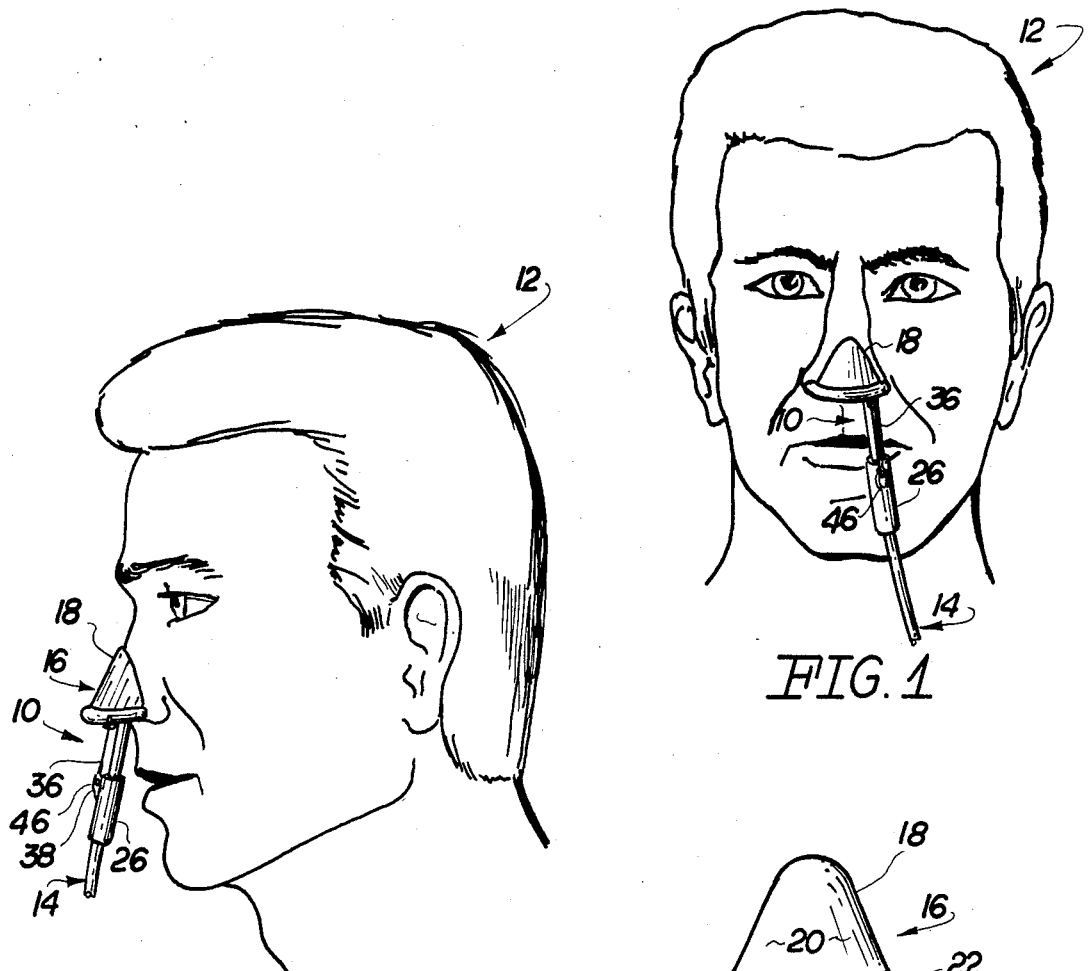
FIG. 1
FIG. 2
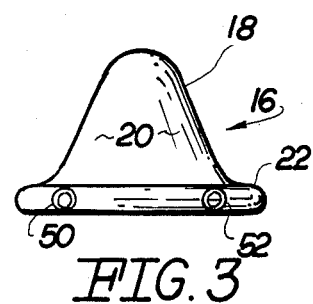
FIG. 3
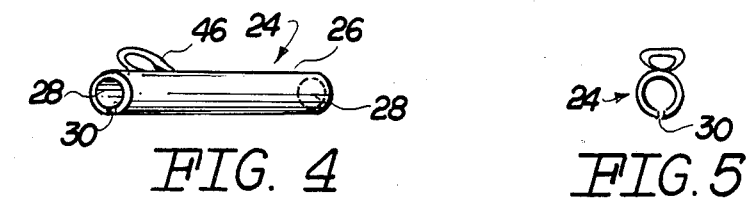
FIG. 4  FIG. 5
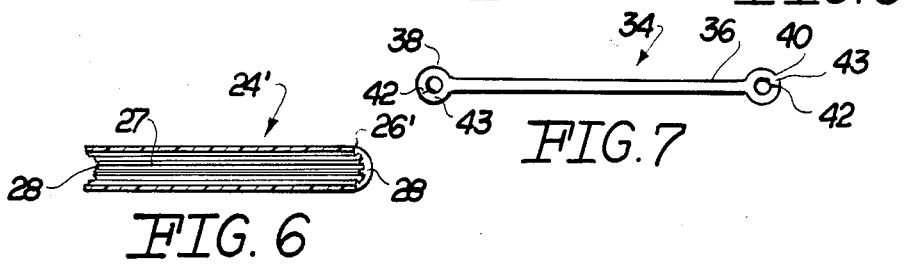
FIG. 6  FIG. 7

ANCHOR DEVICE FOR GASTROINTESTINAL TUBE

BACKGROUND OF THE INVENTION

1. Field of the Invention

An anchoring assembly or structure allowing for normal inadvertent and purposeful selective displacement, for purposes of adjustment, of a gastrointestinal tube relative to the nose as the tube passes through one nostril of the nose along the gastrointestinal tract without causing irritation to portions of the patients body engaging the tube or the assembly.

2. Description of the Prior Art

In the treatment of patients it is common practice to use a gastrointestinal tube commonly referred to as a SALEM TUBE for entering the gastrointestinal tract of the patient by initially passing the tube into the nostril and further there along. While placement and operation of such drainage tubes is of course quite common and effective, certain problems are recognized in the medical profession regarding efficient, safe and comfortable mounting or placement of such tubes especially since such tubes are frequently maintained in their operative position for extended periods.

It is well recognized that certain disadvantages associated with the use of gastrointestinal tubes involve irritation to the outer skin surface of the patient by any type of adhesive or similar securement device which effectively secures the tube to the patient as the tube enters one of the nostrils of the nose. A typical means for accomplishing this is merely wrapping adhesive about the outer surface of the tube and similarly securing the same adhesive strip or material to the outer surface of the nose. The normal movement of the patient sometimes causes nasal septal ulcers and/or necrosis by allowing excessive tube movement while the tube is in direct contact with an inner portion of the nose such as when the tube is continuously repositioned or as set forth above, due to the normal movement of the patient.

The prior art has attempted to overcome problems of the type set forth above through the provision of specific anchoring or mounting structures. While operable for their intended function numerous ones of these prior art devices have been found to be overly complicated, somewhat difficult or time consuming in their installation or removal from the patient and thereby nessesitating the requirement of extensive nursing care by repositioning or readjusting the tube properly into its operative position. The following United States patents are representative of patented prior art devices attempting to overcome certain of the problems set forth above.

Gordon, U.S. Pat. No. 2,590,000 discloses a mounting device which while operative may be considered somewhat cumbersome or less then totally efficient. For example, components 7 and 8 are composed of hooks or open eyelets and as such pose a problem with becoming inmeshed in clothing, sheets, pillow cases, etc. Also, dislodgement of the device is a distinct possibility when patients are asleep or sedated and turn in bed from side to side.

Hill, U.S. Pat. No. 3,046,989 utilizes an adhesive substance to hold both the tube and to fix the nasal device to the nose. Repositioning of the tube for any reason necessitates the adhesive assembly around the tube to be removed and resecured. It is also recognized that the prolonged use of conventional adhesive tape on the nasal portion of the device can conceivably cause skin irritation. Also, the adhesive component surrounding the tube, if removed and repositioned repeatedly can lose its adhesive qualities thereby requiring replacement of the entire unit.

Moor, U.S. Pat. No. 4,120,340 includes a structure which utilizes adhesive components and requires threading in some manner through the tube coupling device. The utilization of such a device is time consuming for nursing personnel caring for the patient.

Even in view of prior art structures of the type set forth above there is still a need in the medical profession for a simple, easily positional and safe anchoring device or assembly which allows some minimal "normal" movement of the tube relative to the nose and nostril through which it enters. However, excessive movements relative thereto is prevented so as to reduce the possibility of ulcers or irritation to portions of the nose, skin, etc. disposed in direct contact with the tube. Also the mounting member of a preferred assembly should be formed of a material which, may adhere directly to the outer skin but which reduces the possibility of skin irritation through the provision of a "breathable" air permeable material cooperating with the other structural components of a preferred assembly to eliminate the need for frequent or repeated repositioning. Therefore, valuable nursing time would be saved both in the initial mounting of the device on the patient and he elimination of the need for constant repositioning thereof.

SUMMARY OF THE INVENTION

The present invention relates to an anchoring assembly specifically of the type to anchor or secure a gastrointestinal tube in its intended and operative position relative to the nose and more specifically an entry nostril of the patient in such a manner that minimal, "normal" movement of the tube relative to the patient, while in its operative position is permitted yet excessive movement is prohibited. The subject anchoring assembly comprises a mounting member conforming, at least in part, to a portion of the outer surface of the nose and secured thereto as by adhesive. The mounting member reduces the possibility of skin irritation frequently caused by conventional adhesive substance or material, such as adhesive tape, by forming the mounting member from an air permeable or "breathable" material.

A securement means preferably in the form of a substantially elongated sleeve having opposite open ends communicating with a hollow interior of the sleeve along its length is secured to the tube itself. Such securement may be defined by removably attaching the sleeve by means of an elongated channel or slit formed therein such that the tube may pass along a portion of its length, into the interior of the sleeve and be gripped thereby due to the normal flexibility or elasticity of the sleeve and the material from which it is formed having somewhat of an inherent memory.

A connecting means in the form of a connecting member is interconnected at opposite ends thereof both to the mounting member secured to the nose of the patient and to the securement means or sleeve secured to the outside of the tube. The securement sleeve is mounted to the tube in spaced relation to the nose and point of entry of the tube into the nostril thereof for operative positioning of the tube along the gastrointestinal tract of the patient.

The length of the connecting sleeve and the fact that it is formed from an elastic material serves to effectively retain the tube by restricting excess movement thereof but at the same time allowing at least minimal displacement of the tube relative to the patient to accommodate the normal movements of the patient. Therefore, by reducing excessive movement of the tube relative to the patient the skin and/or portions of the nose coming in direct contact with the exterior surface of the tube will have less of a chance to be irritated by continuous rubbing therebetween.

Therefore, the following advantages exist due to the cooperative nature of the structural components of the subject assembly and their positioning and cooperative placement on the patient in order to removably retain the gastrointestinal tube in its intended and operative position. Elimination of skin irritations is accomplished by utilizing material which allows the skin to effectively "breath". The subject assembly reduces or effectively eliminates nasal septal ulcers and/or necrosis by allowing enough tube movement to prevent the above but prohibiting excessive tube movement which would require repositioning. The subject assembly is easily adaptable to all commercially available gastrointestinal tube diameters thereby negating manufacture of various sizes of the subject device depending on tube diameter. The structural components of the subject assembly allows its mounting, by medical personnel in seconds and further acquires a minimal amount of nursing care thereby freeing nurses for the more important functions of patient care. Rapid tube repositioning, if required, is accomplishable without the necessity of disassembling or disconnecting the various components from one another.

The invention accordingly comprises the features of the construction, combination of elements and arrangement of parts which will be exemplified in the construction hereinafter set forth, and the scope of the invention will be indicated in the claims.

BRIEF DESCRIPTION OF THE DRAWINGS

For a fuller understanding of the nature of the present invention, reference should be had to the following detailed description taken in connection with the accompanying drawings in which:

FIG. 1 is a front plan view of the assembly of the present invention mounted on a patient so as to operatively position a gastrointestinal tube.

FIG. 2 is a side view of the embodiment of the subject assembly of FIG. 1 in its operative position on a patient.

FIG. 3 is a top view showing interior details and connectors of a mounting member portion of the present invention.

FIG. 4 is a securement sleeve designed to grip the tube itself in spaced relation to the mounting member of FIG. 3.

FIG. 5 is an end view of the embodiment of FIG. 4.

FIG. 6 is a longitudinal sectional view showing interior details of another embodiment of the securement sleeve.

FIG. 7 is a detailed view of the connecting element serving to interconnect the mounting member and the securement sleeve as set forth above.

Like reference numerals refer to like parts throughout the several views of the drawings.

DETAILED DESCRIPTION OF PREFERRED EMBODIMENT

As shown in FIGS. 1 and 2 the anchoring assembly is generally indicated as 10 and is shown in its assembled and operative position on a patient 12 and interconnected to a gastrointestinal tube 14 of the type known as a SALEM TUBE manufactured by Sherwood Medical Company of St. Louis, Mo. Specifically, the subject assembly 10 is useable with other commercially available gastrointestinal tubes and is meant to accommodate tubes of varying sizes. As further shown in FIGS. 4 through 7 the assembly 10 of the present invention comprises a mounting member 16 including a cover or cap portion 18 disposed in secured mounted position over outer skin surface portion of the nose of the patient 12 as clearly shown in FIGS. 1 and 2.

The interior or engaging confrontational surface 20 of the mounting member 16 may, in a preferred embodiment, include an adhesive coating material over at least a portion thereof so as to adhere the cap 18 in the positions shown in FIGS. 1 and 2. An important feature of the present invention is the formation of the material from which the cap or cover 18 is formed to have air permeable or "breathable" characteristics thereby allowing air to pass into the surface being covered by the cap 18 and into direct exposure to the skin surface exposed to the adhesive on the inner surface 20. In addition, such material may be permeable to moisture or water vapor. By virtue of this material, skin irritation due to prolonged contact with adhesive material will be substantially reduced or eliminated thereby insuring greater comfort to the patient. The mounting member 16 further includes a malleable material strip 22 which may be formed of a light weight metal, such as aluminum, which is bendable or capable of being shaped into at least an outer surface configuration of a portion of the nose. By virtue of the provision of this reinforcement strip 22 greater integrity of the cover member 16 is provided and in fact the cover member 18 is more adhesively adhered to its operative position for prolonged periods of time.

The assembly of the present invention further comprises a securement means generally indicated as 24 in both FIGS. 4 and 5. The securement means comprises a substantially elongated sleeve 26 having opposite open ends 28 and a hollow interior as clearly shown in FIG. 5. Further, an integrally formed channel or slit extends along the length of the sleeve 26 as at 30 and is provided to allow the passage therethrough of a portion of the length of the tube 14 into the interior of the sleeve 26 such that the sleeve may effectively grip about the outer surface of the tube 14. The material from which the sleeve 26 if formed may be resilient to the extent that it contains a certain amount of inherent memory. Accordingly, when the tube 14 is forced into the interior of the sleeve 26 through the elongated channel or slit 30, the sleeve will form its normal position as shown in FIG. 5 and thereby be disposed in somewhat gripping engagement with the outer surface of the tube 14. It is important therefore that the transverse dimension of the channel or slit 30 is somewhat less then the transverse dimension of the tube 14 so that the sleeve 26 may properly grip a round the outer surface of the tube 14. However, the relative dimensions of the sleeve 26 and the tube 14 are such as to allow manual positioning of the sleeve along the length of the tube 14 but inadvertent relative movement there between, as due to slippage, will be resisted.

Another embodiment of the sleeve 26 is shown in FIG. 6 wherein the securement means 24' includes a sleeve 26' having a plurality of spaced apart substantially parallel ribs 27 formed along the length thereof on the interior surface. Such ribs protrude outwardly from the interior surface of the sleeve 26' into engagement with the outer surface of the tube 14. This will serve to accommodate tubes of varying transverse dimension and eliminate the need to construct the securement sleeve 26 in varying sizes.

The assembly 10 of the present invention further comprises a connecting means generally indicated as 34 and being defined by a connecting element 36 having a substantially elongated configuration and formed of an elastic or stretchable material. The connecting element 36 has opposite ends 38 and 40 which may be structured into a generally "eyelet" configuration including a central aperture 42. Each of the eyelets 38 and 40 may have a opening as at 43 formed therein to allow the respective eyelets 38 and 40 to be connected to one of a plurality of connectors. As shown in FIGS. 1 and 2 the connecting element 36 is secured at its opposite ends to the securement sleeve 36 and to the mounting member 16. By such interconnecting attachment, the connecting element 36, at least in part due to its resiliency, serves to effectively retain the placement or position of the securement sleeve 26 and therefore the tube 14 to which it is attached relative to the entry of the tube 14 into the nose or through either nostril thereof. In order to accomplish removable interconnection of the connecting element 36 to both the securement sleeve 26 and to the mounting member 16, an attachment means is provided. Such attachment means includes a first connector 46 secured to the outer surface of the securement sleeve 26 and removably attachable to the one of the opposite ends 38 or 40. Such removable attachment is accomplished by passing a peripheral portion of the first connector 46 into the interior of one of the oppositely disposed eyelet ends 38 or 40 through the appropriate opening 43 as set forth above.

The attachment means further comprises a second and third connectors 50 and 52 respectively. These connectors 50 and 52 are disposed along the under or bottom portion of the mounting member 16 each in alignment with one of the nostrils of the nose. Therefore, the opposite end of the connecting element 36 not attached to the securement sleeve 26 is attached to one of the second or third connectors 50 or 52 depended upon which nostril is intended to carry or have the gastrointestinal tube 14 passed therethrough into the gastrointestinal tract. Either of the connectors 50 and 52 are removably attached to the appropriate opposite ends as at 40 by passing through opening 43.

It is therefore to be understood that the following claims are intended to cover all of the generic and specific features of the present invention herein described, in all statements of the scope of the invention which is a matter of language, might be said to fall therebetween.

Now that the invention has been described, what is claimed is:

1. An anchoring assembly for securing a gastrointestinal tube in operative position to a patient, said assembly comprising:
   (a) a mounting member structured to at least partially enclose and removably engage an outer skin surface of the nose and including a major portion thereof formed of a flexible, air permeable material and configured to allow passage of the tube into either nostril of the nose,
   (b) securement means removable connected to the tube at a location spaced from the nose for securing the tube in a preferred, spaced position from the nose of the patient,
   (c) said securement means comprising an elongated sleeve having a hollow interior portion and open opposite ends communicating therewith and a channel extending along the length of the sleeve and having a transverse dimension less than the transverse dimension of the tube and being structured to allow adjustable placement of the tube within said hollow interior portion,
   (d) a connecting means attached in interconnecting relation between said mounting member and said sleeve for connecting the tube to the mounting member in a preferred, adjustable, spaced apart operative location relative to the nose,
   (e) said connecting means comprising a connecting element having an elongated configuration and formed of an elastic material and being connected at opposite ends thereof to said sleeve and said mounting member, said sleeve being adjustably mounted and positionable on the tube, said connecting element, due to its elasticity, being movable with said sleeve and the tube relative to the mounting member,
   (f) an elongated malleable material reinforcement strip disposable substantially transversely to the length of the nose and selectively conformable into a configuration corresponding to the outer surface of the nose, said reinforcement strip secured to said mounting member and disposed to facilitate conformance of said mounting member to the surface of the nose, and the tube being both displaceable and retained relative to the nose of the patient and selectively adjustable relative thereto by manual manipulation of the sleeve relative to the tube by medical personnel.

2. An assembly as in claim 1 wherein said mounting member comprises an inner surface being removably and adhesively secured to the exterior skin surface of the nose.

3. An assembly as in claim 1 further comprising attachment means secured to both said securement means and said mounting member for connecting respective ones of opposite ends of the connecting element to said securement means and said mounting member.

4. An assembly as in claim 1 wherein said attachment means comprises a first connector affixed to said securement means and structured for removable attachment to one end of said connecting elements.

5. An assembly as in claim 1 wherein said sleeve is formed from a flexible material having an inherent memory and dimensioned and configured to removable grip the tube along a portion of its length.

6. An assembly as in claim 1 further comprising cushion means disposed between the inner surface of said mounting member and an outer surface of the nose and in protective relation thereto.

7. An assembly in claim 6 wherein said cushion means is formed in aligned relation to an under surface of said reinforcement member and is configured to extend along the length thereof.

8. An assembly as in claim 1 wherein said malleable material is aluminum.

9. An anchoring assembly for securing a gastrointestinal tube in operative position to a patient, said assembly comprising:
(a) a mounting member structured to at least partially enclose and removably engage an outer skin surface of the nose and including a major portion thereof formed of a flexible, air permeable material and configured to allow passage of the tube into either nostril of the nose,
(b) securement means removably connected to the tube at a location spaced from the nose for securing the tube in a preferred, spaced position from the nose of the patient,
(c) said securement means comprising an elongated sleeve having a hollow interior portion and open opposite ends communicating therewith and a channel extending along the length of the sleeve and having a transverse dimension less than the transverse dimension of the tube and being structured to allow adjustable placement of the tube within said hollow interior portion of the sleeve,
(d) a connecting means attached in interconnecting relation between said mounting member and said sleeve for connecting the tube to the mounting member in a preferred, adjustable, spaced apart operative location relative to the nose,
(e) said connecting means comprising a connecting element having an elongated configuration and formed of an elastic material and being connected at opposite ends thereof to said sleeve and said mounting member, said sleeve being adjustably mounted and positioned on the tube, said connecting element, due to its elasticity, being movable with said sleeve and the tube relative to the mounting member,
(f) attachment means comprising a first connector affixed to said sleeve and a second and third connector affixed to said mounting member each in aligned registry with a different nostril of the patient's nose,
(g) each of said first, second and third connectors structured for removable attachment to a correspondingly positioned end of said connecting element, said second and third connectors disposed for independent connection to a common corresponding positioned end of said connector element for positioning of the tube in different nostrils of the nose of the patient, and
(h) the tube being both displaceable and retained relative to the nose of the patient and selectively adjustable relative thereto by manual manipulation of the sleeve relative to the tube by medical personnel.

* * * * *